US00PP22994P2

(12) United States Plant Patent
Kerley et al.

(10) Patent No.: US PP22,994 P2
(45) Date of Patent: Aug. 28, 2012

(54) ***VIOLA* PLANT NAMED 'KERVIOPRISE'**

(50) Latin Name: *Viola×wittrockiana*
Varietal Denomination: Kervioprise

(76) Inventors: David Kerley, Cambridge (GB); Priscilla Grace Kerley, Cambridge (GB); Timothy Edward Kerley, Cambridge (GB)

( * ) Notice: Subject to any disclaimer, the term of this patent is extended or adjusted under 35 U.S.C. 154(b) by 0 days.

(21) Appl. No.: 13/065,127

(22) Filed: Mar. 14, 2011

(51) Int. Cl.
*A01H 5/00* (2006.01)

(52) U.S. Cl. ..... Plt./323

(58) Field of Classification Search ..... Plt./323
See application file for complete search history.

*Primary Examiner* — Annette Para
(74) *Attorney, Agent, or Firm* — Cassandra Bright

(57) ABSTRACT

A new and distinct *Viola×wittrockiana* cultivar named 'KERVIOPRISE' is disclosed, characterized, by a unique combination of a large, round "pansy" type flower, found on a trailing plant. Flower color is white, flushed with violet color. Plants have a compact, trailing plant habit. The new variety is a *Viola×wittrockiana*, suitable for outdoor landscape and container use.

2 Drawing Sheets

Figure 1:
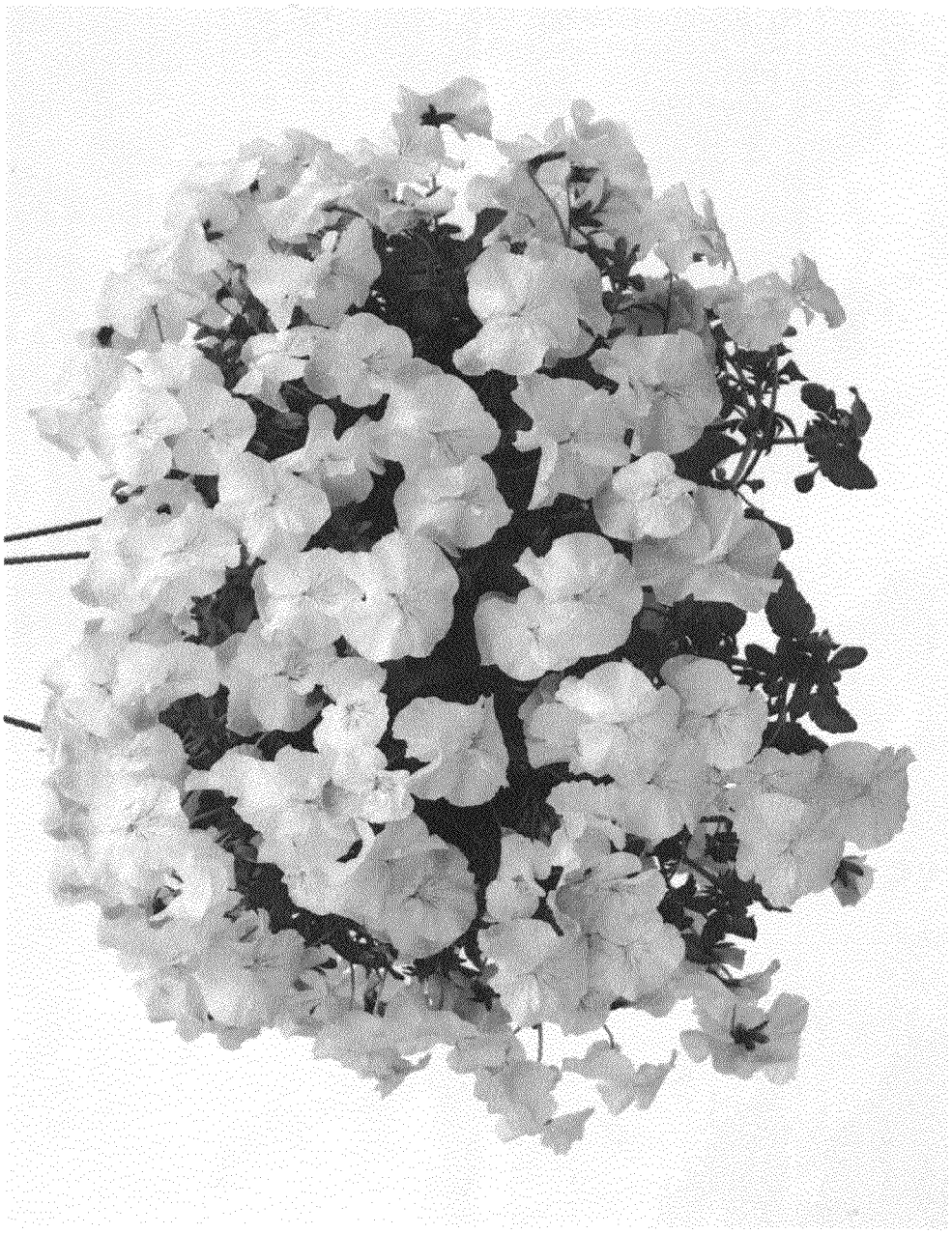

Latin name of the genus and species: *Viola×wittrockiana.*
Variety denomination: 'KERVIOPRISE'.

BACKGROUND OF THE INVENTION

The new cultivar is the product of a planned breeding program under the direction of the inventors, David Kerley, Priscilla Kerley and Timothy Kerley, all citizens of the United Kingdom. The objective of the breeding program was to produce new trailing *Viola×wittrockiana* cultivars for commercial ornamental purposes. The new cultivar resulted from an open pollination crossing the unpatented proprietary seed parent, referred to as '05-32-1' and unknown proprietary pollen varieties. The exact date of the cross resulting in 'KERVIOPRISE' is unknown, but most likely during 2005. The selection of the new variety 'Kervioprise' was made in April 2006, by the inventors at a research greenhouse located in Cambridge, UK.

Asexual reproduction of the new cultivar 'KERVIOPRISE' by vegetative cuttings was first performed at the same research greenhouse in Cambridge, UK in July of 2006, and has shown that the unique features of this cultivar are stable and reproduced true to type in successive generations.

SUMMARY OF THE INVENTION

The cultivar 'KERVIOPRISE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KERVIOPRISE' These characteristics in combination distinguish 'KERVIOPRISE' as a new and distinct *Viola* cultivar:

1. Unique round "pansy" flower, on a trailing *Viola* plant, rather than the elongated flower form more commonly found on spreading or trailing types which are usually *Viola×williamsii.*
2. Large flower.
3. Spreading, trailing plant habit.

4. Exceptionally compact habit when grown in a small pot.
5. White flower color with *Violet* tones.

PARENT COMPARISON

Plants of the new cultivar 'KERVIOPRISE' are similar to plants of the seed parent variety, in most horticultural characteristics. However, plants of the new cultivar produce larger flowers, of a white coloration, with violet tones, whereas the seed parent has purple flowers. Additionally, the new variety produces a plant with a more trailing habit than the seed parent, and somewhat undulating, rather than frilly flower petals.

Plants of the new cultivar 'KERVIOPRISE' cannot be compared to the pollen parent, as a result of the open pollination, the pollen parent is not known.

COMMERCIAL COMPARISON

Plants of the new cultivar 'KERVIOPRISE' are similar to plants of the commercial variety known as *Viola* 'Sunviolaho' U.S. Plant Pat. No. 17,677, in some horticultural characteristics. However, plants of the new cultivar 'KERVIOPRISE' produce a larger, rounder flower, with some undulation to the petals, rather than flat petals. Additionally, the new variety has shorter peduncles, and Violet coloration in the upper petal not found in 'Sunviolaho'.

Plant of 'KERVIOPRISE' can also be compared to the commercial variety *Viola* 'Flovelwh' U.S. Plant Pat. No. 20,762. Plants are similar in most horticultural characteristics, however, 'KERVIOPRISE' produces a larger flower, with a more trailing plant habit. Additionally, plants of 'KERVIOPRISE' produce flowers with a Violet coloration to the upper petal, not found in 'Flovelwh'.

BRIEF DESCRIPTION OF THE PHOTOGRAPHS

The accompanying photograph in FIG. 1 illustrates in full color typical plants of 'KERVIOPRISE' grown in a poly house in Cambridge, UK. Plants are approximately 35 weeks old shown in a 20 cm basket, 3 rooted cuttings were planted per pot.

Figure 2:
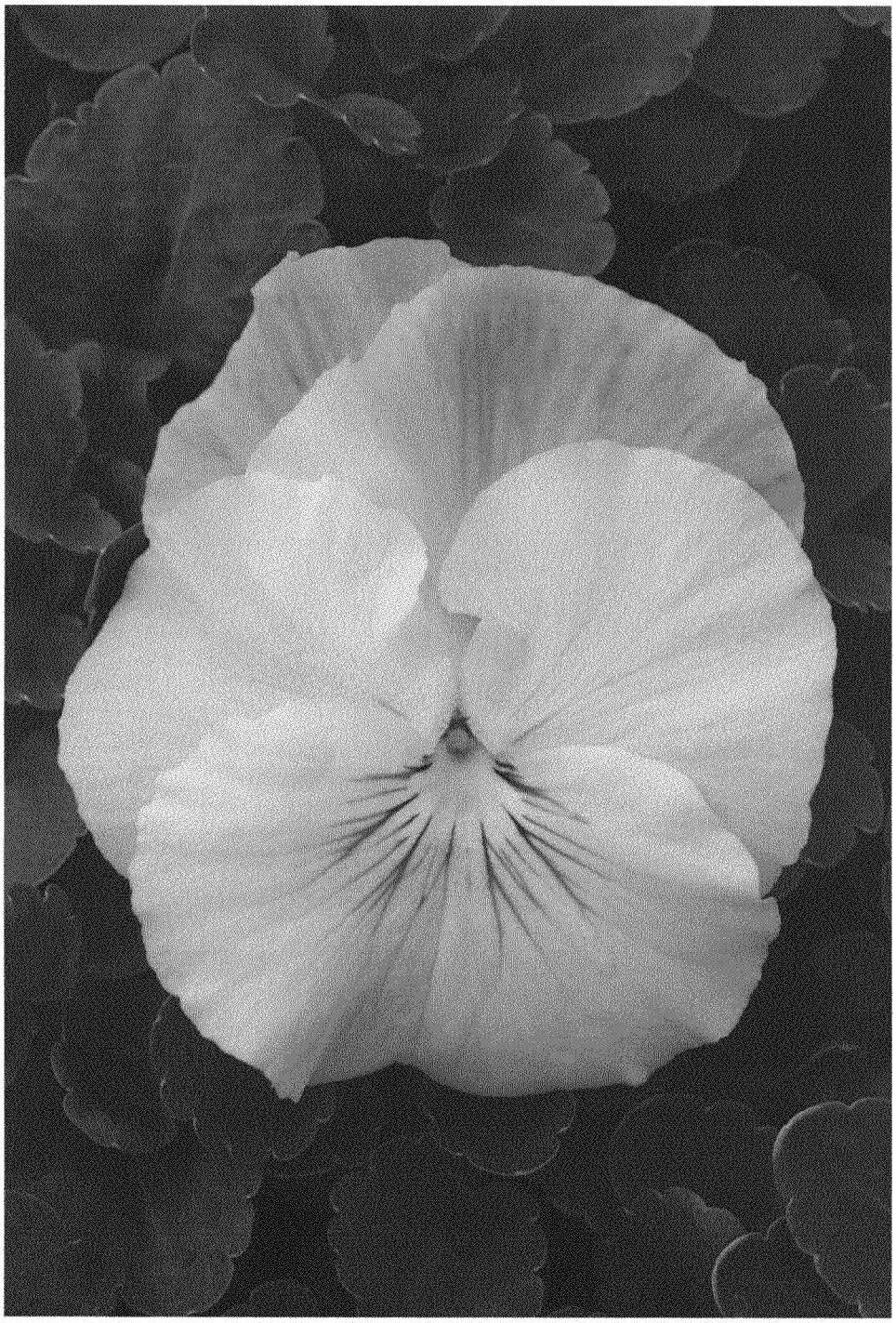

FIG. 2 illustrates a close up of a typical flower of 'KERVOIPRISE'. The photographs were taken using conventional weeks old shown in a 20 cm basket, 3 rooted cuttings were planted per pot. FIG. 2 illustrates a close up of a typical flower of 'KERVOIPRISE'. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 1995 except where general terms of ordinary dictionary significance are used. The following observations and measurements describe 'KERVIOPRISE' plants grown in an unheated poly house in Cambridge, UK. The growing temperature ranged from approximately −5 to 12° C. at night to −2 to 18° C. during the day. 3 rooted cuttings were planted in a 20 cm basket. No chemical or photoperiodic treatments were given. Measurements and numerical values represent averages of typical flowering types.

Botanical classification: *Viola×wittrockiana* 'KERVIOPRISE.'

Age of the plant described: Approximately 37 weeks, in a 20 cm basket.

PROPAGATION

Time to rooting: About 15 to 20 days at approximately 20° C.

Root description: Fine, fibrous.

PLANT

Growth habit: Spreading, trailing.

Height: Approximately 13 cm.

Plant spread: Approximately 75 cm.

Branching characteristics: Free branching.

Diameter of lateral branches: Approximately 0.6 cm.

Length of lateral branches: Approximately 35 cm.

Texture of lateral branches: Glabrous.

Internode length: Approximately 3 cm.

Strength of stem: Strong.

Color of lateral branches: Near RHS Yellow-Green 144B.

Quantity of lateral and sub lateral branches: Approximately 80.

FOLIAGE

Leaf:

*Arrangement*.—Alternate.

*Average length*.—Approximately 3.4 cm.

*Average width*.—Approximately 2.4 cm.

*Shape of blade*.—Obovate.

*Apex*.—Rounded.

*Base*.—Cordate.

*Attachment*.—Petioled.

*Margin*.—Crenulate.

*Texture of top surface*.—Glabrous.

*Texture of bottom surface*.—Glabrous.

*Color*.—Developing foliage upper side: Near R.H.S. Green 137A. Developing foliage under side: Near R.H.S. Yellow-Green 147B. Mature foliage upper side: Near R.H.S. Yellow-Green 147A. Mature foliage under side: Near R.H.S. Yellow-Green 147B.

*Venation*.—Type: Pinnate. Venation color upper side: Near R.H.S. Yellow-Green 144A. Venation color under side: Near R.H.S. Yellow-Green 144B.

Petiole:

*Length*.—Approximately 1.6 cm.

*Diameter*.—0.2 cm.

*Color*.—Near RHS Yellow-Green 144B.

FLOWER

Bloom period: Naturally blooming March to November under United Kingdom outdoor conditions.

Inflorescence: Form: Single, axillary flowers, comprised of 5 petals total; 2 upper, 2 lateral and 1 lower in a single whorl.

Flower longevity on plant: About 5 days.

Persistent or self-cleaning: Self-Cleaning.

Fragance: Slight.

Flowers per plant: Approximately 160.

Flower bud:

*Bud color*.—Near RHS Green-White 157A with slightly varying venation color, either Violet-Blue 96B, Violet-Blue 93B or 93C.

*Bud length*.—Approximately 2 cm.

*Bud diameter*.—Approximately 0.9 cm.

Individual flower:

*Flower size*.—Length: Approximately 7.1 cm. Width: Approximately 7.0 cm.

*Petal texture*.—All petals, glabrous, velvety with matte appearance.

Petals:

*Upper petals*.—Shape: Orbicular. Length: Approximately 3.9 cm. Width: Approximately 4.8 cm. Margin: Entire. Apex: Rounded. Aspect: Somewhat undulating.

*Color*.—When opening, upper surface: Whiter than RHS White 155C; Flushed Purple-Violet 82B. Flush sometimes absent. When opening, lower surface: Whiter than 155C; flushed Violet 86B; veins Violet 87D. Flush sometimes absent. Fully opened, upper surface: Whiter than RHS White 155C; flushed Purple-Violet 82C. Flush sometimes absent. Fully opened, lower surface: Whiter than RHS White 155C; flushed Purple-Violet 88C between veins. Flush sometimes absent.

*Lateral petals*.—Shape: Reniform. Length: Approximately 3.6 cm. Width: Approximately 4.3 cm. Margin: Entire. Apex: Rounded.

*Color*.—When opening, upper surface: Near RHS White 155C, base near Violet-Blue 93D. When opening, lower surface: Near RHS White 155C. Fully opened, upper surface: Whiter than 155C; occasionally ray at base Violet 87D; eye Yellow 9A. Fully opened, lower surface: Whiter than RHS 155C.

*Lower petal*.—Shape: Very broad obocordate to orbicular. Length: Approximately 3.7 cm. Width: Approximately 5.1 cm. Margin: Entire. Apex: Rounded.

*Color*.—When opening, upper surface: Near RHS 155C; ray at base Violet 89D or Violet-Blue 95C; eye Yellow 14A. When opening, lower surface: Near RHS White 155C, ray at base near Green 136C. Fully opened, upper surface: Whiter than 155C; ray at base Violet 88A, 88B 88C; all colors can be present; eye Yellow 17A. Fully opened, lower surface: Whiter than 155C, base Yellow 12B.

Additional flower data:

*Spur on flower petal*.—Length: Approximately 0.7 cm. Width: Approximately 0.2 cm. Depth: Approximately 0.3 cm. Color: Near RHS Yellow-Green 148C.

*Eye dimensions*.—Length: Approximately 0.7 cm. Width: Approximately 0.4 cm.

Sepals:

*Quantity*.—5.
*Arrangement*.—Whorled.
*Length*.—Approximately 2 cm.
*Width*.—Approximately 0.6 cm.
*Color*.—Near RHS Green 137B.
*Shape*.—Elliptic.
*Apex*.—Acute.
*Base*.—Obtuse.
*Texture*.—Glabrous.

Peduncle:

*Peduncle length*.—Approximately 13 cm.
*Peduncle diameter*.—Approximately 0.3 cm.
*Aspect*.—Upright with outward curve.
*Color*.—Near RHS Yellow-Green 146A.
*Texture*.—Glabrous.

REPRODUCTIVE ORGANS

*Stamen quantity*.—Approximately 5.
*Filament length*.—Approximately 0.1 cm.
*Anther length*.—Approximately 0.4 cm.
*Anther color*.—Near RHS Yellow-White 158B, tip Greyed-Orange 167A.
*Pollen color*.—Near RHS Yellow 10D.
*Pollen amount*.—Scant to moderate.
*Pistil length*.—Approximately 0.7 cm.
*Style length*.—Approximately 0.2 cm.
*Style color*.—Near RHS Yellow-Green 150D.
*Stigma shape*.—Bulbous with concave depression on uppermost portion.
*Ovary color*.—Near RHS Yellow-Green 145C.
*Stigma color*.—Near RHS Yellow-Green 151C.

OTHER CHARACTERISTICS

Disease resistance: Neither resistance nor susceptibility to diseases or pests has been observed in this variety.

Temperature tolerance: Tolerates high temperature to at least 35° C. Tolerates low temperatures to −10° C.

Fruit/seed production: Fruit and seed production not observed.

What is claimed is:

1. A new and distinct cultivar of *Viola* plant named 'KERVIOPRISE'as herein illustrated and described.

* * * * *